United States Patent [19]

Uphues et al.

[11] Patent Number: 4,866,193
[45] Date of Patent: Sep. 12, 1989

[54] PURIFICATION OF PHOSPHOROUS ACID ESTERS

[75] Inventors: Guenter Uphues, Monheim; Uwe Ploog, Haan, both of Fed. Rep. of Germany

[73] Assignee: Henkel Kommanditgesellschaft auf Aktien, Duesseldorf, Fed. Rep. of Germany

[21] Appl. No.: 133,585

[22] Filed: Dec. 16, 1987

[30] Foreign Application Priority Data

Dec. 20, 1986 [DE] Fed. Rep. of Germany ....... 3643761

[51] Int. Cl.$^4$ .................................................. C07F 9/9
[52] U.S. Cl. ..................................... 558/150; 558/146
[58] Field of Search ................................. 558/146, 150

[56] References Cited

U.S. PATENT DOCUMENTS 2,818,421 12/1957 Max ...................................... 558/150
4,587,063 5/1986 Kurosaki et al. ................... 558/146

OTHER PUBLICATIONS

Houben-Weyl, Methoden der Organischen Chemie, 1964, p. 156 et seq.
Chemical Abstract, 95:221794w.

*Primary Examiner*—Anton H. Sutto
*Attorney, Agent, or Firm*—Ernest G. Szoke; Wayne C. Jaeschke; Henry E. Millson, Jr.

[57] ABSTRACT

Process for the purification of phosphoric acid partial ester mixtures in which, after the addition of a basic, non-volatile inorganic or organic compound, the unreacted fatty alcohol is directly removed from the partial ester mixture by distillation.

13 Claims, No Drawings

PURIFICATION OF PHOSPHOROUS ACID ESTERS

BACKGROUND OF THE INVENTION

1. Field of the Invention:

This invention relates to the purification of phosphoric acid partial ester mixtures produced by reaction of fatty alcohols with phosphorus pentoxide.

2. Statement of Related Art:

Among the phosphoric acid esters produced worldwide, the mixtures of mono- and dialkyl derivatives obtained by reaction of phosphorus pentoxide with alcohols are predominant.

The reaction mechanism has not yet been definitively elucidated. Similarly, the summation formula currently postulated for phosphorus pentoxide, namely $-P_4O_{10}-$, is not yet certain.

T. Fay, G. P. Sheridan and D. R. Karsa, Kommittee Espanol dea Detergentes, XII. Jornado (1981), point out that the phosphorus pentoxide normally marketed contains large amounts of high-polymer material and, accordingly, should retain the formula $P_2O_5$.

In the production of phosphoric acid esters, especially by reaction of fatty alcohols with phosphorus pentoxide, the products contain varying amounts-depending on the molar reaction ratio of unreacted alcohol which, in many cases, affects the use of the products and is therefore almost always undesirable. The removal of the free alcohol is only possible by complicated, timeconsuming measures.

K. Sasse in "Houben-Weyl", Vol. 12, "Organische Phosphorverbindungen (Organic Phosphorus Compounds)", Part 2, pages 156 et seq describes the formation of phosphoric acid partial esters by the action of alcohols on phosphorus pentoxide. The free phosphoric acid is normally separated from the reaction product via the barium salts or, where relatively long-chain alcohols are used, via the sodium salts. The phosphorylation of sugars with phosphorus pentoxide is carried out at elevated temperature in the presence of tertiary amines.

Direct separation of the free alcohol by distillation is complicated by the elimination of olefins from the esters. In the case of short-chain alcohols, olefin formation actually becomes the main reaction. Chemical Abstracts, 95, 22 1704 w describes the neutralization of aliphatic phosphoric acid esters with an aqueous alkanolamine solution and subsequent extraction of the nonionic material with a low-boiling paraffin.

Published German Application 33 25 337 describes a process for the production of phosphoric acid diesters in which a base is added to the partial ester mixture in a quantity of from 0.5 to 1.3 equivalents, based on the phosphorus atoms in the mixture. The phosphoric acid monoesters are converted into o-phosphoric acid and organic hydroxyl compounds by hydrolysis in aqeous solution and, after the reaction step, are removed by distillation in the case of low-boiling alcohols or by fractional crystallization in the case of relatively long-chain alcohols. Phosphoric acid diesters which may still contain free unreacted alcohol are obtained.

STATEMENT OF THE INVENTION

Other than in the operating examples, or where otherwise indicated, all numbers expressing quantities of ingredients or reaction conditions used herein are to be understood as modified in all instances by the term "about".

An object of the present invention is to provide a simple process which enables the alcohol still present in phosphoric acid ester mixtures to the removed without decomposition of the esters formed. It has now surprisingly been found that there is virtually no formation of oelfins if small quantities (0.05 to 0.2 mol equivalents, based on the quantity of phosphorus atoms in the mixture) of a basic, non-volatile inorganic or organic compound are added to the partial ester mixture before or preferably after the reaction and the unreacted fatty alcohol is directly removed from the mixture by distillation. In this way, the thermal stability of the phosphoric acid esters is so comprehensively increased that even relatively long-chain fatty alcohols can be removed from the mixture by distillation. The thermal stability of the phosphoric acid esters is still intact even at temperatures of from 180° to to 200° C.

The present invention provides a process for the purification of phosphoric acid partial esters which are produced in known manner by reaction of a fatty alcohol or fatty alcohol mixture with phosphorus pentoxide. Fatty alcohols in the context of the invention are $C_6-C_{18}$ saturated or unsaturated alcohols and, more particularly, straight-chain or branched-chain $C_8-C_{12}$ alcohols. Fatty alcohols according to the invention are selected from the group comprising hexyl alcohol, 2-ethylhexyl alcohol, heptyl alcohol, octyl alcohol, nonyl alcohol, isononyl alcohol, decyl alcohol, isodecyl alcohol, undecyl alcohol, dodecyl alcohol, tridecyl alcohol, isotridecyl alcohol, tetradecyl alcohol, pentadecyl alcohol, hexadecyl alcohol, heptadecyl alcohol, octadecyl alcohol, oleyl alcohol, elaidyl alcohol and isostearyl alcohol.

In view of the high boiling points of the alcohols used, the distillation is preferably carried out at reduced pressure. More preferably, the distillation is carried out at 0.1 to 50 mbar.

The basic (i.e. alkaline) non-volatile, inorganic or organic compounds added to the partial ester mixture in quantities of from 0.05 to 0.2 mol equivalents, based on the phosphorus atoms in the mixture, are selected from alkali metal hydroxides, such as potassium hydroxide and sodium hydroxide, and alkanolamines and amines with molecular weights in the range of from 129 to 297. By "non-volatile" is meant not volatile under the reaction conditions employed in the practice of the invention. Examples of alkanolamines and amines in the above molecular weight range include diethanolamine, dimethyl cocosamine, cocosamine, tributylamine and N-lauryldiaminopropane.

The basic compounds are preferably added to the partial ester mixtures in quantities of 0.1 mol equivalent, based on the phosphorus atoms in the mixture.

The advantages of the present invention become clear on analysis of the distillate. Without the addition of the basic, nonvolatile compounds according to the invention, the quantities of distillate are increased in relation to the process of the invention. In addition, without the addition of the basic, nonvolatile compounds, the iodine value of the distillate is increased by a factor of at least ten.

The invention will be illustrated but not limited by the following examples.

EXAMPLES

Example A 594.0 g (4.5 moles) n-octanol (OH value 424) were introduced into heated in a 1000 ml three-necked flask equipped with a stirrer and thermometer. At a temperature of 50° to 60° C., 213.0 g (1.5 moles) phosphorus pentoxide were uniformly added over a of 2 h using a hermetically sealed powder dispenser. The mixture was then left to react for 2 h at 90° C. After addition of 31 g water, the mixture was stirred for another 3 h at 90° C.

837 g of a colorless oil was obtained. Analysis (passage over an ion exchanger) revealed a content of 7.8% unreacted alcohol.

Example 1

16.6 g (0.07 mole) dimethyl cocosamine were added to 200.0 g (0.72 equivalent P) of the phosphoric acid ester obtained in accordance with Example A, followed by distillation in vacuo. The mixture was heated to a sump temperature of 170° C. under a pressure of 20 mbar. 15.2 g distillate having an iodine value of 1.6 were obtained. 199.8 g of an almost colorless residue containing 0 2% n-octanol remained in the flask.

Under the same conditions, the following results were obtained:

| Example | Addition | Mol/P | Distillate quantity (g) | IV. | Residue quantity (g) |
| --- | --- | --- | --- | --- | --- |
| 2 | potassium hydroxide | 0.1 | 14.8 | 1.3 | 187.9 |
| 3 | diethanolamine | 0.2 | 14.1 | 1.1 | 186.3 |
| 4 | cocosamine | 0.2 | 13.8 | 1.5 | 208.1 |
| 5 | tributylamine | 0.1 | 13.1 | 1.4 | 194.4 |
| 6 | N—lauryldi-aminopropane | 0.1 | 14.9 | 3.1 | 193.7 |

Comparison Example 1

200.0 g of the phosphoric acid ester obtained in accordance with Example A were also subjected to the distillation treatment in vacuo in the absence of an addition according to the invention.

After only 23.8 g distillate had accumulated, heating was stopped although distillation was not yet over. Analysis of the distillate revealed an iodine value of 15; the quantity of residue amounted to 175.2 g for a residual content of 2.4% n-octanol.

Example B 231.0 g (1.75 moles) n-octanol (OH value 425) were reacted with 71.0 g (0.5 mole) phosphorus pentoxide in a 500 ml three-necked flask equipped as in Example 1. The reaction temperature during the 2-hour addition was 80 to 90° C. After stirring for 2 h at 100° C., 11.1 g water were added, followed by stirring for another 3 h.

312g of a yellowish colored oil still containing 14.8% n-octanol were obtained.

Example 7

30.4 g (0.2 mol/P) dimethyl cocosamine were added to 200.0 g of the phosporic acid ester obtained in accordance with Example B, followed by vacuum distillation at 20 mbar to remove the unreacted alcohol. The maximum sump temperature was 172°. In all, 28.8 g distillate having an iodine value of 2.0 were formed.

Comparison Example 2

200.0 g of the ester obtained in accordance with Example B were treated as in Example 7 without the addition of dimethyl cocosamine. 34.2 g distillate having an iodine value of 46.3 were formed.

Example C 780 g (6 moles) 2-ethyl hexanol were reacted with284 g (2moles) phosphorus pentoxide at 50° to 60° C. in a 2-liter three-necked flask equipped as in Example A. After stirring for 2 hours, 36 g water were added and the mixture treated therewith for 3 hat 90° C.

1103g of a yellowish liquid still containing 13% unreacted alcohol were obtained.

Example 8

0.2 mole potassium hydroxide/P in the form of a 45% solution were added to 550 g of the ester obtained in accordance with Example C.

The free alcohol was distilled off under a pressure of 20 mbar up to a sump temperature of 160° C.

70.2 g distillate having an iodine value of 1.2 were obtained.

EXAMPLE D 390 g (1.5 moles) tallow alcohol were reacted with 71 g (0.5 mole) phosphorus pentoxide at 60° to 70° C. in a 1-liter three-necked flask equipped as in Example A. After stirring for 2 h at 70° C., 10 g water were added and the mixture kept at 90° C. for 3 h.

471 g of a white mass solid at room temperature, which still contained 18.1% unreacted alcohol, were obtained.

Example 9

200 g of the ester obtained in accordance with Example D were mixed with 10.1 g (0.1 mole/P) dimethyl cocosamine and the resulting mixture passed through a thin-layer evaporator at 180° C. under a pressure of $10^{-1}$ bar.

38.4 g distillate, iodine value 1.3, were obtained.

We claim:

1. A process for the preparation and purification of phosphoric acid partial ester mixtures comprising the steps of:
   A. reacting at least one $C_6$-$C_{18}$ fatty alcohol with phosphorus pentoxide, optionally in the presence of from about 0.05 to about 0.2 mole equivalents, based on phosphorus atoms in the reaction mixture, of at least one basic non-volatile inorganic or organic compound, to produce a reaction mixture containing phosphoric acid partial esters and unreacted fatty alcohol:
   B. adding to the reaction mixture obtained in step A from about 0.05 to about 0.2 mole equivalents, based on phorphorus atoms in the reaction mixture, of at least one basic non-volatile inorganic or organic compound where such compound is not added in step A; and
   C. removing unreacted fatty alcohol from the reaction mixture by distillation.

2. The process of claim 1, wherein at least one basic non-volatile inorganic or organic compound is added in step B.

3. The process of claim 1 wherein the at least one basic non-volatile inorganic or organic compound is at least one of an alkali metal hydroxide, or an alkanolamine or amine having a molecular weight in the range of from 129 to 297.

4. The process of claim 2 wherein the at least one basic non-volatile inorganic or organic compound is at least one of an alkali metal hydroxide, or an alkanolamine or amine having a molecular weight in the range of from 129 to 297.

5. The process of claim 3 wherein the basic non-volatile inorganic or organic compound is sodium hydroxide and/or potassium hydroxide.

6. The process of claim 3 wherein the basic non-volatile inorganic or organic compound is present in a quantity of about 0.1 mole equivalent.

7. The process of claim 1 wherein the $C_6$-$C_{18}$ fatty alcohol is at least one of: hexyl alcohol, 2-ethylhexyl alcohol, heptyl alcohol, octyl alcohol, nonyl alcohol, isononyl alcohol, decyl alcohol, isodecyl alcohol, undecyl alcohol, dodecyl alcohol, tridecyl alcohol, isotridecyl alcohol, tetradecyl alcohol, pentadecyl alcohol, hexadecyl alcohol, heptadecyl alcohol, octadecyl alcohol, oleyl alcohol, elaidyl alcohol, and isostearyl alcohol.

8. The process of claim 1, wherein the at least one $C_6$-$C_8$ fatty alcohol contains from 8 to 18 carbon atoms.

9. The process of claim 1, wherein step C is carried out in vacuo.

10. The process of claim 9 wherein in step C a pressure of from about 0.1 to about 50 mbar is employed.

11. The process of claim 1 wherein step C is carried out at a sump temperature of up to about 200° C.

12. In a process for the preparation and purification of phosphoric acid partial esters comprising reacting fatty alcohols with phosphorus pentoxide to produce a reaction mixture containing phosphoric acid partial esters and unreacted fatty alcohol, the improvement comprising adding to the reactants from about 0.05 to about 0.2 mole equivlents, based on phosphorus atoms in the reaction mixture, of at least one basic non-volatile inorganic or organic compound, and thereafter removing unreacted fatty alcohol from the reaction mixture by distillation.

13. In a process for the preparation and purification of phosphoric acid partial esters comprising reacting fatty alcohols with phosphorus pentoxide to produce a reaction mixture containing phosphoric acid partial esters and unreacted fatty alcohol, the improvement comprising adding to the reaction mixture from about 0.05 to about 0.2 mole equivalents, based on phosphorus atoms in the reaction mixture, of at least one basic non-volatile inorganic or organic compound, and thereafter removing unreacted fatty alcohol from the reaction mixture by distillation.

* * * * *